(12) United States Patent
Griffis (10) Patent No.: US 10,328,172 B2
(45) Date of Patent: Jun. 25, 2019

(54) SCENTED ATTACHMENT FOR CONTAINERS

(71) Applicant: SZENT CO., Santa Monica, CA (US)

(72) Inventor: Shawn Griffis, La Jolla, CA (US)

(73) Assignee: SZENT CO., Santa Monica, CA (US)

( * ) Notice: Subject to any disclaimer, the term of this patent is extended or adjusted under 35 U.S.C. 154(b) by 0 days.

(21) Appl. No.: 15/663,534

(22) Filed: Jul. 28, 2017

(65) Prior Publication Data
US 2017/0326263 A1    Nov. 16, 2017

Related U.S. Application Data (63) Continuation of application No. 13/429,300, filed on Mar. 23, 2012, now abandoned.
(Continued)

(51) Int. Cl.
   *A61L 9/00*     (2006.01)
   *A61L 9/12*     (2006.01)
   (Continued)

(52) U.S. Cl.
   CPC ............ *A61L 9/12* (2013.01); *A61L 9/048* (2013.01); *B65D 1/0246* (2013.01);
   (Continued)

(58) Field of Classification Search
   CPC .. B65D 2203/12; B65D 23/00; B65D 51/245; B65D 75/5855; A23L 1/22008; B65B 7/12; B65B 27/18; A61L 9/12; A61L 9/048
   (Continued)

(56) References Cited

U.S. PATENT DOCUMENTS

| | | |
|---|---|---|
| D28,746 S | 5/1898 | Blount |
| D30,338 S | 3/1899 | Mann |
| (Continued) | | |

FOREIGN PATENT DOCUMENTS

| | | |
|---|---|---|
| DE | 102006038257 A1 | 2/2008 |
| DE | 102009020524 A1 | 11/2010 |
| (Continued) | | |

OTHER PUBLICATIONS

High-Tech Cocktail Glass Lets You Experience Plain Water as the Perfect Cocktail, Oddity Central, available at http://www.odditycentral.com/technology/high-tech-cocktail-glass-lets-you-experience-plain-water-as-the-perfect-cocktail.html, Nov. 20, 2017.
(Continued)

*Primary Examiner* — Ernesto A Grano
(74) *Attorney, Agent, or Firm* — Perkins Coie LLP (57) ABSTRACT

Aspects of the disclosure include an attachment for providing a scent to a container. The scented attachment may be configured for being associated with a container, such as a drink or a food storage container. In one instance, the attachment is of a size or shape so as to fit around a circumference of the container. In another instance, the attachment may be configured for being associated to the container with a suitable attachment mechanism. For instance, the attachment may include a substrate having a first surface comprising an attachment mechanism for associating the scented attachment to the container; and a second surface comprising a scent. Systems including a scented attachment and a container, including their methods of use, are also provided.

19 Claims, 8 Drawing Sheets

Related U.S. Application Data (60) Provisional application No. 61/467,888, filed on Mar. 25, 2011.

(51) Int. Cl.
| | | |
|---|---|---|
| *B65D 51/24* | (2006.01) | |
| *B65D 17/28* | (2006.01) | |
| *A61L 9/04* | (2006.01) | |
| *B65D 1/02* | (2006.01) | |
| *B65D 23/14* | (2006.01) | |
| *B65D 41/34* | (2006.01) | |

(52) U.S. Cl.
CPC ......... *B65D 17/4012* (2018.01); *B65D 23/14* (2013.01); *B65D 41/34* (2013.01); *B65D 51/245* (2013.01); *A61L 2209/15* (2013.01); *B65D 2517/0013* (2013.01); *B65D 2517/0056* (2013.01); *B65D 2517/5091* (2013.01)

(58) Field of Classification Search
USPC ....................................................... 220/694
See application file for complete search history.

(56) References Cited

U.S. PATENT DOCUMENTS

| | | | |
|---|---|---|---|
| D32,681 S | 5/1900 | Morgenthaler | |
| D44,392 S | 7/1912 | Whitney | |
| D159,985 S | 9/1950 | Heisey | |
| D172,090 S | 5/1954 | Pree | |
| 3,043,464 A * | 7/1962 | Cerasari | A61J 9/00 |
| | | | 215/11.1 |
| D206,889 S | 2/1967 | Benes | |
| 3,409,181 A | 11/1968 | McDonnell | |
| D230,187 S | 1/1974 | Schultz | |
| D256,003 S | 7/1980 | Barr | |
| 4,540,721 A | 9/1985 | Staller | |
| D288,902 S | 3/1987 | Lewis | |
| 4,687,203 A | 8/1987 | Spector | |
| 4,717,017 A | 1/1988 | Sprinkel et al. | |
| D319,035 S | 8/1991 | Kruse | |
| 5,165,603 A | 11/1992 | Hahn | |
| 5,249,676 A | 10/1993 | Ashcraft et al. | |
| D348,836 S | 7/1994 | McCallum et al. | |
| 5,477,640 A * | 12/1995 | Holtkamp, Jr. | A01G 27/04 |
| | | | 239/289 |
| D372,765 S | 8/1996 | Sisk | |
| D374,837 S | 10/1996 | Austin | |
| 5,635,229 A | 6/1997 | Ray | |
| D394,824 S | 6/1998 | Itzkowitz | |
| 5,795,644 A | 8/1998 | Delarosa | |
| 6,006,472 A * | 12/1999 | Holtkamp, Jr. | A61L 9/127 |
| | | | 47/79 |
| 6,045,833 A | 4/2000 | Landau | |
| 6,102,224 A | 8/2000 | Sun | |
| 6,112,749 A * | 9/2000 | Hall | A61J 11/003 |
| | | | 128/898 |
| 6,290,914 B1 * | 9/2001 | LeJeune | A01M 1/2088 |
| | | | 422/123 |
| D453,000 S | 1/2002 | Shinjo | |
| D457,783 S | 5/2002 | Bodum | |
| D468,492 S | 1/2003 | Wilhelm | |
| 6,511,726 B1 * | 1/2003 | Kinigakis | A61L 9/04 |
| | | | 428/40.1 |
| D501,625 S | 2/2005 | Biggerstaff | |
| 7,005,152 B2 | 2/2006 | Landau | |
| D533,747 S | 12/2006 | Jin | |
| D533,802 S | 12/2006 | Thompson et al. | |
| D534,428 S | 1/2007 | Reed et al. | |
| D535,210 S | 1/2007 | Park | |
| D545,235 S | 6/2007 | Carter-Smith et al. | |
| 7,284,711 B2 * | 10/2007 | Reed | A61L 9/12 |
| | | | 239/289 |
| 7,470,035 B1 | 12/2008 | Benitez | |
| D587,118 S | 2/2009 | Sadiq et al. | |
| 7,484,675 B2 * | 2/2009 | Brown | A61L 9/12 |
| | | | 222/192 |
| D592,950 S | 5/2009 | Kopulos | |
| D600,115 S | 9/2009 | Trayser | |
| D614,247 S | 4/2010 | Clausen | |
| D615,816 S | 5/2010 | Joy et al. | |
| D617,426 S | 6/2010 | Zeyfang | |
| 7,748,557 B2 | 7/2010 | Robinson | |
| D635,352 S | 4/2011 | Himley et al. | |
| D646,600 S | 10/2011 | Minkkinen et al. | |
| D662,767 S | 7/2012 | Hotell et al. | |
| 8,364,028 B1 | 1/2013 | Vaske et al. | |
| 8,440,265 B2 | 5/2013 | Duan | |
| 8,474,637 B2 | 7/2013 | Zhang et al. | |
| D696,952 S | 1/2014 | Sawicki et al. | |
| 8,708,189 B2 | 4/2014 | Reitzig | |
| D734,670 S | 7/2015 | Griffis | |
| D752,975 S | 4/2016 | Gatto | |
| D753,490 S | 4/2016 | O'Donahue | |
| 9,302,830 B2 | 4/2016 | Ramsey et al. | |
| D776,529 S | 1/2017 | Torrison et al. | |
| D791,591 S | 7/2017 | Berge | |
| D795,021 S | 8/2017 | Lindloff | |
| 9,801,969 B2 | 10/2017 | Griffis | |
| D807,173 S | 1/2018 | Cooper et al. | |
| 2002/0139093 A1 | 10/2002 | Landau | |
| 2002/0190023 A1 | 12/2002 | Landau | |
| 2005/0196571 A1 | 9/2005 | Penny et al. | |
| 2006/0246265 A1 | 11/2006 | Rogers et al. | |
| 2006/0278542 A1 | 12/2006 | Pham et al. | |
| 2006/0278543 A1 | 12/2006 | Pham | |
| 2006/0291756 A1 | 12/2006 | Thomas et al. | |
| 2007/0023301 A1 | 2/2007 | Pham | |
| 2009/0078786 A1 | 3/2009 | Slade | |
| 2009/0098026 A1 * | 4/2009 | Wood | A61L 9/122 |
| | | | 422/123 |
| 2009/0155505 A1 | 6/2009 | Wagenheim | |
| 2009/0258118 A1 | 10/2009 | Gillian | |
| 2010/0323134 A1 | 12/2010 | Bostian et al. | |
| 2011/0253584 A1 | 10/2011 | Duan | |
| 2012/0006909 A1 | 1/2012 | Zhang et al. | |
| 2013/0043245 A1 | 2/2013 | Griffis | |
| 2013/0056551 A1 | 3/2013 | Zhang et al. | |
| 2013/0062239 A1 | 3/2013 | Key | |
| 2013/0105066 A1 | 5/2013 | Landau | |
| 2013/0276339 A1 | 10/2013 | Hernandez et al. | |
| 2015/0027974 A1 | 1/2015 | Niec | |
| 2015/0329247 A1 | 11/2015 | Lou | |
| 2017/0239382 A1 | 8/2017 | Griffis | |
| 2018/0043047 A1 | 2/2018 | Griffis | |

FOREIGN PATENT DOCUMENTS

| | | |
|---|---|---|
| DE | 202017001221 U1 | 7/2017 |
| WO | 2010068731 | 6/2010 |
| WO | 2018085580 | 5/2018 |
| WO | 2018203993 | 11/2018 |

OTHER PUBLICATIONS

Flavour Bottle: The world's first flavored bottle, available at https://www.kickstarter.com/projects/flavourtechnologies/flavour-bottle-the-worlds-first-flavored-bottle/description.

Etsy. Mini Orange Plastic Soda Bottle Rings/Safety Seals. Mar. 23, 2018 [earliest online date], [site visited Apr. 23, 2018]. Available from Internet, <URL:https://etsy.me/2HSzu7f>. (Year: 2018).

The New York Times. Mystery in Sochi Doping Case Lies With Tamper-Proof Bottle by Rebecca R. Ruiz. May 13, 2016 [earliest online date], [site visited Apr. 23, 2018]. Available from Internet, <URL:https://www.nytimes.com/2016/05/14/sports/russia-doping-bottles-olympics-2014.html>. (Year: 2016).

Forever Gifts. Beveled Edge Black Tungsten Wedding Band. Apr. 26, 2017 [earliest online date], [site visited Apr. 26, 2018]. Available from Internet, <URL:https://www.forevergifts.com/beveled-edge-black-tungsten-wedding-band-free-engraving/>. (Year: 2017).

(56) References Cited

OTHER PUBLICATIONS

International Search Report and Written Opinion for International Application No. PCT/US18/24630, dated Apr. 23, 2018 (7 pages).
Non-Final Office Action for U.S. Appl. No. 29/598,879, dated May 1, 2018 (26 pages).
Non-Final Office Action for U.S. Appl. No. 29/298,882, dated May 1, 2018 (29 pages).
First Action Interview Pilot Program Pre-Interview Communication for U.S. Appl. No. 15/782,720, dated Apr. 2, 2018 (6 pages).
Examination Report received for European Union Design Application No. 005826559; dated Nov. 28, 2018 (2 pages).
Non-Final Office Action received for U.S. Appl. No. 15/663,534, dated Aug. 16, 2018 (26 pages).
First Examiner's Report received for Australian Application No. 2018202261; dated Aug. 30, 2018 (5 pages).
First Examiner's Report received for Canadian Application No. 177508; dated Jul. 23, 2018 (3 pages).
Examiner's Report received for Canadian Application No. 2999583; dated Jan. 30, 2019 (3 pages).
Office Action for German Application No. 10 2018 003 090.4, dated Jan. 15, 2019 (8 pages).

\* cited by examiner

SCENTED ATTACHMENT FOR CONTAINERS

CROSS-REFERENCE TO RELATED APPLICATIONS

This application is a continuation of U.S. patent application Ser. No. 13/429,300 entitled "SCENTED ATTACHMENT FOR CONTAINERS" and filed on Mar. 23, 2012, which claims the benefits and priority of U.S. Provisional Application No. 61/467,888, entitled "SCENTED ATTACHMENT FOR CONTAINERS", which was filed on Mar. 25, 2011. The entire contents of the aforementioned patent applications are incorporated by reference as part of the disclosure of this application.

BACKGROUND

The nasal cavity has specialized sensory cells that mediate olfaction. The main olfactory system of humans and animals detects volatile chemicals, and the accessory olfactory system detects fluid-phase chemicals. Olfaction like taste is a form of chemoreception. The chemicals that activate the olfactory system, generally at very low concentrations, are called odorants. Accordingly, there is a commonality between the perception of smell and the perception of taste. In fact, in certain instances, the sense of smell may supplement and/or otherwise enhance the sense of taste. For instance, it is well known that maladies affecting the sense of smell adversely affect the sense of taste. As taste plays an important role in ones motivation for consuming a food or drink article, there is an interest in the art for agents that enhance the perception of taste of food and drink articles. The present disclosure meets these and other such needs.

SUMMARY OF THE DISCLOSURE

Aspects of the disclosure include an attachment for providing a scent to a container. In certain instances, the scented attachment is configured for being associated with a container, such as a drink or a food storage container. The scented attachment may be associated with the container in any suitable manner. In one instance, the scented attachment is of a size or shape so as to fit around a circumference of the container. Thus, the scented attachment may be a sleeve, a wrap, a ring, or the like. In another instance, the scented attachment may be configured for being associated to the container with a suitable attachment mechanism. For instance, the scented attachment may include a substrate having a first and a second surface. The first surface comprises an attachment mechanism for associating the scented attachment to the container; and a second surface comprises a scent. In such a manner, a scented agent may be associated with a food or drink container so as to enhance the perception of the taste of the food or drink contained therein, thereby, enhancing the experience and/or one's motivation in eating or drinking. For instance, the substrate comprises a ring having an opening configured for receiving a portion of a bottle therein, wherein the ring is removably associated with a lid which lid is configured for being sealably associated with a bottle, and wherein when the lid is removed from the bottle the lid separates or detaches from the ring thereby releasing the scent. In one instance, a container comprises a body for holding matter, the body being enclosed on all sides except an opening; a scented attachment provided on the body near the opening; and a cap that removably covers the opening. Also provided is a method for its use and a system for providing a scent to a container that includes a scented attachment, as described herein, and a container that is configured for being associated with the container.

BRIEF DESCRIPTION OF THE DRAWINGS

According to common practice, the various features of the drawings may not be drawn to-scale. Rather, the dimensions of the various features may be arbitrarily expanded or reduced for clarity. Included in the drawings are the following figures:

FIGS. 1A and 1B illustrate instances of a scented ring in accordance with the disclosure, in which FIG. 1A represents one instance of the scented ring.

FIGS. 2A and 2B illustrate instances of a scented strip in accordance with the disclosure, in which

Before the present disclosure is further described, it is to be understood that this disclosure is not limited to particular instances described, as such may of course vary. It is also to be understood that the terminology used herein is for the purpose of describing particular instances only, and is not intended to be limiting. Unless defined otherwise, all technical and scientific terms used herein have the same meaning as commonly understood by one skilled in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications are cited. The disclosures of these publications, patents and published patent applications referenced in this application are hereby incorporated by reference in their entirety into the present disclosure. Citation herein by the Applicant of a publication, patent, or published patent application is not an admission by the Applicant of said publication, patent, or published patent application as prior art.

It must be noted that as used herein and in the appended claims, the singular forms "a", "and", and "the" include plural referents unless the context clearly dictates otherwise. Thus, for example, reference to an "opening" may include a plurality of such openings, and reference to "the gripping element" includes reference to one or more gripping elements and equivalents thereof known to those skilled in the art, and so forth. It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

DETAILED DESCRIPTION

Aspects of the disclosure include an attachment for providing a scent to a container. In certain instances, the attachment is a ring or a sticker that is configured for removable association with a container, such as a food or a drink container. In one instance, the ring is configured for wrapping around a portion of the container. In another instance, the sticker is configured for being removably stuck onto a portion of the container. The attachment is configured such that during use of the container having the scented attachment, a subjects' olfactory system is activated by the scent of the attachment, which thereby enhances the sensation, e.g., the perception of taste, of eating or drinking the food or drink item that is contained within the container.

In one instance, the ring includes a circular body with a lumen, wherein the body is configured for being removably associated with a container. For instance, the scented ring includes a stretchable body that is adapted for being fit over a portion of the container. In certain embodiments, the body of the ring is comprised of an elastic material that deforms in a manner such that the diameter of the ring may increase when a stretching force is applied to the ring and/or return to its normal state once the stretching force has been removed. In a manner such as this, the ring may be fit over a portion of the container, such as a neck of a bottle, so as to enhance the perception of consuming the item contained within the container.

In another instance, the attachment may be configured as a sticking element and may include a substrate having a first and a second surface. The first surface may include an attachment mechanism for associating the scented attachment to the container; and a second surface comprises a scent. The attachment surface may include an adhesive or other attachment mechanism, such that it may adhere to a surface of the container. The scented surface may include a matrix configured for releasably holding a scent that may be released there form during the use of the container.

The subject scented attachments of the disclosure will be described first, followed by a description of the methods of their use and the systems in which such scented attachments may be employed. A discussion of representative uses of the subject materials is also presented.

Scented Attachments, Systems and Methods of Use

Figure 1A:
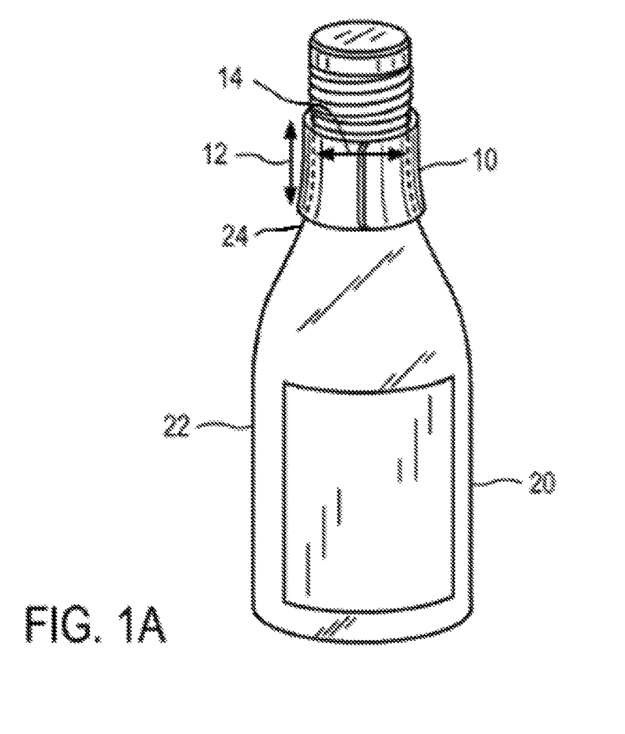
Figure 1B:
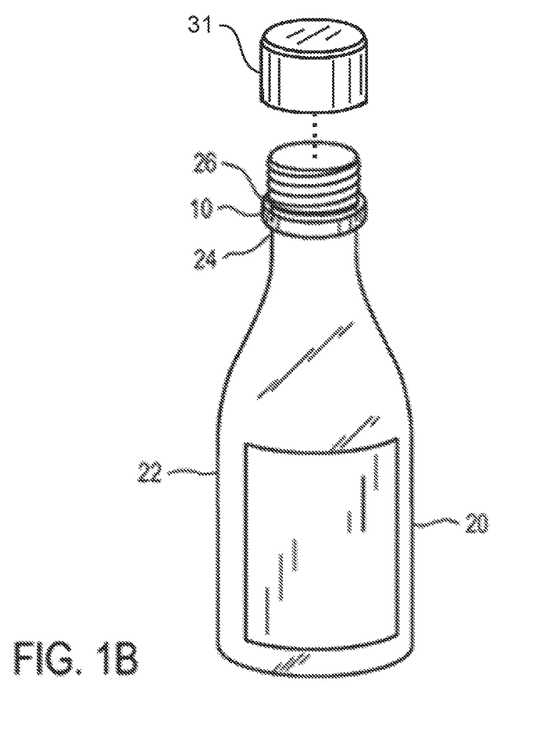
FIG. 1B represents another instance of the scented ring.

As can be seen with respect to FIGS. 1A and 1B, the subject disclosure provides an attachment for providing a scent to an object, such as a container. In one instance, the attachment 10 is a ring that is configured for providing a scent to a container, e.g., a food or drink container 20. By "scent" is meant any agent that is capable of being incorporated within the attachment, being released there from, and stimulating an olfactory sensation of a subject.

For instance, in certain instances, a scent may be a chemical agent that stimulates a chemoreceptor of the olfactory system of the subject or otherwise stimulates sense of smell and/or taste of a subject. For example, in certain instances, a scent may be a volatile compound or odorant, such as a fragrant or other essential oil. Where the scent is a fragrant oil, it may be a food derived oil such as a citrus oil, a mint oil, anise oil, cardamom oil, cinnamon oil, clove oil, coriander oil, eucalyptus oil, fennel oil, lemongrass oil, and/or a nutmeg oil, and the like. The scent may be a citrus oil such as a lemon oil, a lime oil, a neroli oil, and/or an orange oil, and the like. In certain instances, scent comprises a mint oil such as a peppermint oil and/or spearmint oil, and the like.

The scented essential oil may be incorporated within the attachment in any suitable manner. For instance, the attachment may include a matrix within which the essential oil may be incorporated. The matrix may include a liquid or a gel, which may include the scent. The liquid or gel may be associated with the material employed to fabricate the attachment. For example, the attachment may be constructed in any suitable manner and may be fabricated from any suitable material. In certain instances, a suitable material may be one or more of an elastic material, a foamed or vulcanized rubber, neoprene, polyurethane, nylon, lycra, plastic, silicone, and/or a silicone containing material. Hence, the material from which the attachment is produced may be fabricated into a ring or sheet and compression or liquid injection molded into a protective device of the disclosure.

For instance, the body of the attachment may be fabricated using compression molding, during which process an element containing an essential oil is added thereto either during or after the molding process. Additionally, a colorant or other chemical additive may be added to the sheet blanks, which become the compression molded end product, for instance, to color and/or to aid in the release of the product from the mold. In certain instances, the attachment is made from a single piece of shaped or otherwise molded material and may include a cavity into which a scented material, e.g., a gel or substrate containing an essential oil associated therewith is injected or otherwise inserted into the lumen of the scented attachment. The main body of the attachment may comprise elastic properties, such that the attachment can deform to receive a portion of a container, e.g., a neck thereof, and then reform to its original configuration automatically, that is without the need for external manipulation. In certain instances, the attachment may include a main body that is pre-formed into a substrate onto one surface of which a gel or other matrix containing a scented agent, e.g., an essential oil, is added; and to an opposing surface, a suitable attachment mechanism, e.g., an adhesive, is added. One or more removable covers may be added to cover one or more of the scented surface and/or the attachment surface.

The attachment can be made into any desired shape such as a tube, a square or rectangular box, a triangular, pyramidal or circular shape, or the like. And thus the attachment may be configured for fitting around suitable container, such as a round, circular, triangular, square, rectangular, cube shaped container, or the like, and may be of regular or irregular dimensions, so as to fit a variety of bottles, jars, and the like. In certain instances, a scented attachment 10 of the disclosure and the material from which it is fabricated is hygienic, light weight and flexible such that the material is capable of expanding so as to allow the attachment to expand around the contours of the container 20 to be received therein and snuggly fits around the container 20, and yet be configured for returning to its original configuration once the container 20 has been removed from the attachment.

Accordingly, the attachment 10 may be of any suitable size and shape, but is typically of a size and shape so as to be non-obstructively associated with the container 20. The container 20 may be any container such as a container for storing a beverage or other food article. The container 20 may be of any size or any shape, but is typically of a size and a shape suitable for containing a drink or food product, such as a drink or food product that is meant to be readily consumed by a subject. For instance, the container 20 may be a plastic or glass container, a metal or metal alloy container, or the like. If the container 20 is made of glass, the glass may be of any suitable type of glass, such as silicon dioxide, sodalime glass, pyrex, lead crystal, and the like. If the container 20 is made of metal, the metal may be of any suitable type of metal, such as aluminum, steel (e.g., stainless steel), tin, and the like. The container 20 for use in accordance with the subject invention may also include alloys of any suitable metals. The container 20 may also be a plastic container, such as a TUPPERWARE® or RUBBERMAID® or GLAD® container.

The container 20 may contain any material, such as a solid, liquid, or gas. In certain instances, the container 20 is a fluid container that contains a liquid. The liquid within the container may be any form of liquid. In certain embodiments, the liquid is a liquid that is meant to be imbibed. For instance, in certain embodiments, the liquid is a liquid such as, water, soda, a liquid nutrient, a juice, an electrolyte, a sports drink, an alcoholic beverage, and the like. In certain embodiments, the container 20 is a solid object container, for instance, a food container that contains a solid food. For example, the attachment may be configured for being associated with a bottle, a can, a thermos, a camel back container, a canteen, or other such drinking container. In certain instances, the container may be a food container, such as a container for the storage of a food.

The attachment 10 may be associated with the container 20 in any suitable manner. In one instance, the attachment 10 is of a size or shape so as to fit around a circumference of the container 20. Thus, the attachment 10 may be a ring, sleeve, wrap, or the like that has been fabricated in such a manner so as to include a scent therein. For instance, in certain instances, the attachment 10 may be a ring that may be flat or tubular and may include an opening through which a container may be inserted. Accordingly, in certain instances, the ring attachment may be of a size and a shape so as to fit around a portion, e.g., the neck, of a drinking container. The ring, therefore, may have a diameter such that it can slip onto and/or around the neck of a bottle, but not slide down the length of the bottle.

As described above, the attachment 10 may be made of any suitable material, but in certain instances, it is made of a material that is capable of stretching, and thus the diameter of the ring may be configured for moving from a first, smaller diameter to a second, larger diameter when stretched, and/or for returning from the second stretched diameter toward the first, non-stretched diameter in the absence of a suitable stretching force. In a manner such as this, the attachment 10 such as the ring may be configured for fitting snuggly around a portion of the container 20, e.g., the neck, the middle, and/or bottom of the container.

As illustrated in FIG. 1A, the scented attachment 10 can be a ring and may be fabricated as single piece from a unitary material. The material may have a length 14 the matches its width 12, a length 14 less than its width 12, or a length 14 that is greater than its width 12. For instance, in certain embodiments, the length 14 may be in a range from about 2 or 3 mm or less to about 20 cm or more, such as about 5 or 10 mm to about 12 or 15 cm, including about 2 or 5 cm to about 8 to about 10 cm. In certain instances, the ring includes a circumference and the length 14 is measured from one point of a circumference moving in a single direction away from and back to that same point on the circumference. In certain embodiments, dependent on the material from which the ring is made, the length 14 may increase as the material stretches. The width 12 of the material may correspond to that of the length 14 but typically may range from about 2 or 3 mm or less to about 15 cm or more, such as from about 5 or 10 mm to about 12 or 14 cm, including about 2 or 5 cm to about 8 to about 10 cm. The thickness of the material may range from about 1 mm or less to about 10 mm or more, such as from about 2 or 3 mm to about 8 or 9 mm, including from about 4 or 5 mm to about 6 or 7 mm.

In certain instances of the attachment 10 as a ring, as shown in FIG. 1A, the attachment ring may be dimensioned to cover a substantial portion of the neck 24 of a container 20, e.g., a bottle, while leaving the main body 22 uncovered. For instance, where an attachment ring is provided so as to generate a scent detectable by a subject using the container, it may be useful to have an attachment ring that does not cover the entire or even a substantial portion of the body 22 of the container 20, e.g., as this will be less expensive to produce and better for the environment. Accordingly, in one instance, the attachment ring covers all of the neck of the bottle, a top half of the neck of the bottle, or a bottom half of the neck of the bottle. As can be seen with respect to FIG. 1B, in one instance, the scented attachment ring 10 is dimensioned to fit around a top portion 26 of the neck 24 of the container 20. In this instance, the scented attachment ring 10 is configured for covering only the top portion 26 of the neck 24 of the container 20 (e.g., bottle) so as to provide a scent to a person, for instance, while drinking from the container 20. As can be seen with respect to FIG. 1B, a cap 31 associated with the container 20 is removably attachable to the container 20 at the neck 24 to enclose the opening of the container 20 and contain the beverage within the container 20 when attached and to be removed from the opening to allow the beverage to be dispensed from the container 20 when unattached.

Figure 2A:
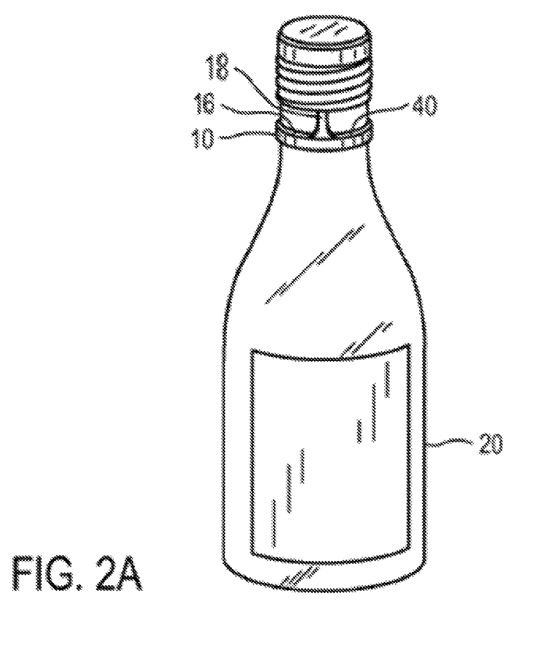
FIG. 2A illustrates a scented strip having a main body and a removable portion with a scented portion within the main body.

FIG. 2A represents another instance of a scented attachment of the disclosure. The attachment 10 includes a main body 16 and a removable portion 18. The main body 16 of the attachment 10 may be configured for encasing a scented strip 40 therein. The scented strip 40 includes a scented agent, e.g., an essential oil, that is associated there with. The removable portion 18 may be removed from the main body 16 of the attachment 10 and thereby release the stored scent encased therein. The removable portion 18 may be associated with a lid of the container or otherwise removable. For instance, when the lid is removed, the removable portion 18 is separated from the main body 16 of the attachment 10, and the scent from scented strip 40 is thereby released. In this configuration, the removable portion 18 may be a tab that may be pulled off by a user prior to drinking, or may be associated with the lid in such a manner that as the lid is removed the tab is removed.

Figure 2B:
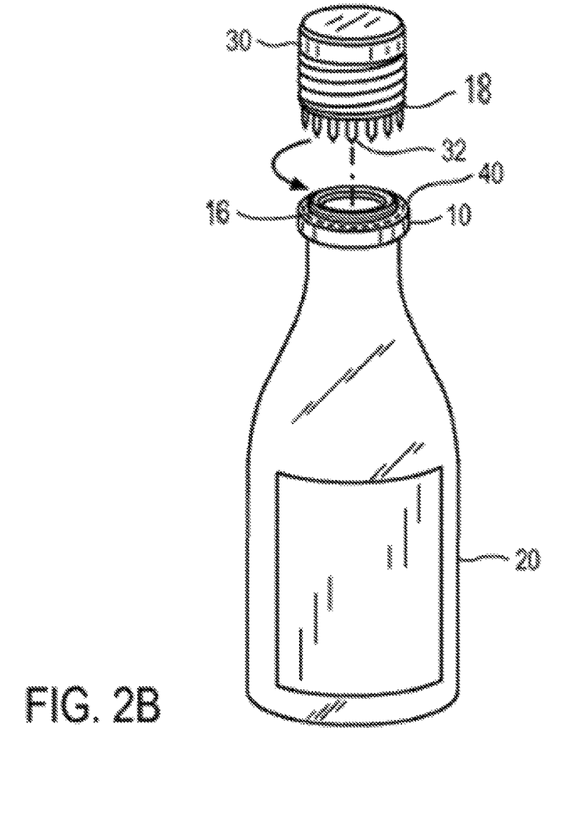
FIG. 2B illustrates an instance of a scented strip having a removable portion that is configured for detachably interacting with a lid of the container.

For instance, as seen with reference to FIG. 2B, the removable portion 18 may be associated with a lid 30 in such a manner that as the lid is removed the removable portion 18 is disassociated from the main body 16 of the attachment 10.

For example, the lid 30 may be configured such that by twisting it relative to the container 20 it may be removed from the container 20, and likewise, the scented attachment 10 may be configured such that as the lid 30 twists, the removable portion 18 also twist relative to the main body 16 along with the lid 30. Thus, as the lid 30 is removed, so is the removable portion 18 and the scented strip 40 is exposed, thereby releasing the scent. In one instance, the lid 30 may include teeth 32 which are associated with the main body 16 and the removable portion 18, such that as the lid 30 is removed the teeth 32 separate from the main body 16 causing the removable portion 18 to be removed from the main body 16.

Figure 3A:
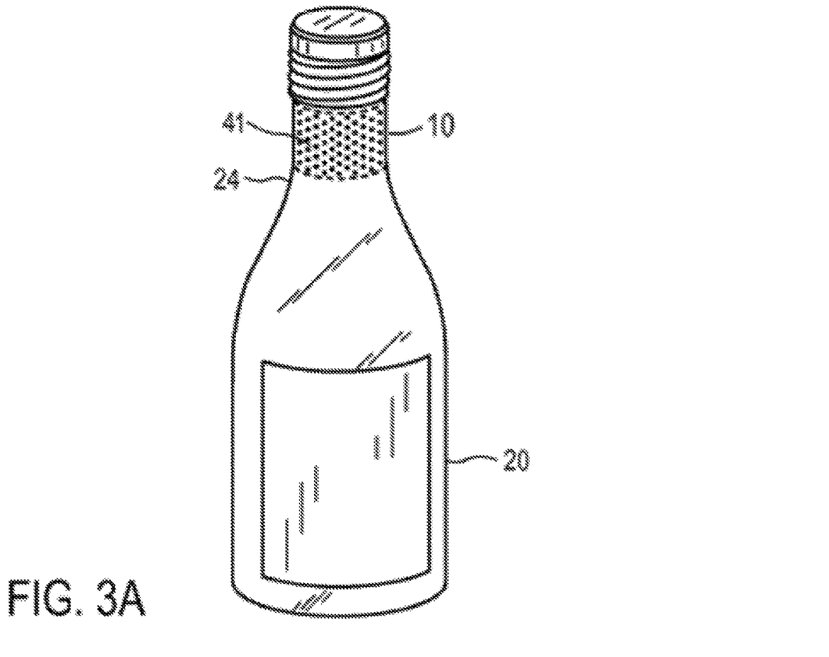
FIG. 3A illustrates another instance of a scented attachment where the scent is integrated into at least a portion of the container.

In certain instances, as with reference to FIG. 3A, the scented attachment 10 may actually be incorporated into the material of the container 20 so as to form a scented area 41. The scented area 41 may be formulated by incorporating an essential oil into the container 20 at an area near the neck 24 of the container 20. A removable cover (not shown) may be placed over the scented area 41 so as to lock in the scent until use. For instance, a user may remove the cover from the scented area 41 prior to opening the container 20 and consuming the drink or food therein.

Figure 3B:
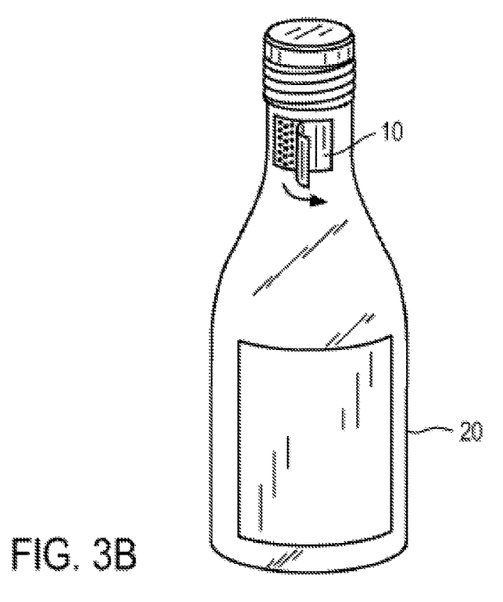
FIG. 3B illustrates another instance of a scented attachment.

FIG. 3B illustrates an instance of a scented attachment 10 wherein the attachment is configured for being associated to the container 20 with a suitable attachment mechanism. For instance, the attachment 10 may include a substrate having a first and a second surface. The first surface comprises an attachment mechanism for associating the scented attachment 10 to the container 20; and a second surface comprises a scent, e.g. an essential oil. The attachment mechanism may be a suitable adhesive, a snap and button configuration, a hook and loop fastener attachment (e.g., Velcro™), and the like. The adhesive may be used to associate the scented attachment 10 to the container 20. Alternatively, a Velcro™ strip may be used to attach the attachment 10 to the container 20. In such a manner the scented attachment 10 may be removable from the container 20. Further, the scented attachment 10 may be a separate element from the container 20, made to be separately obtained and attached thereto, or may be pre-attached to the container 20.

Figure 4:
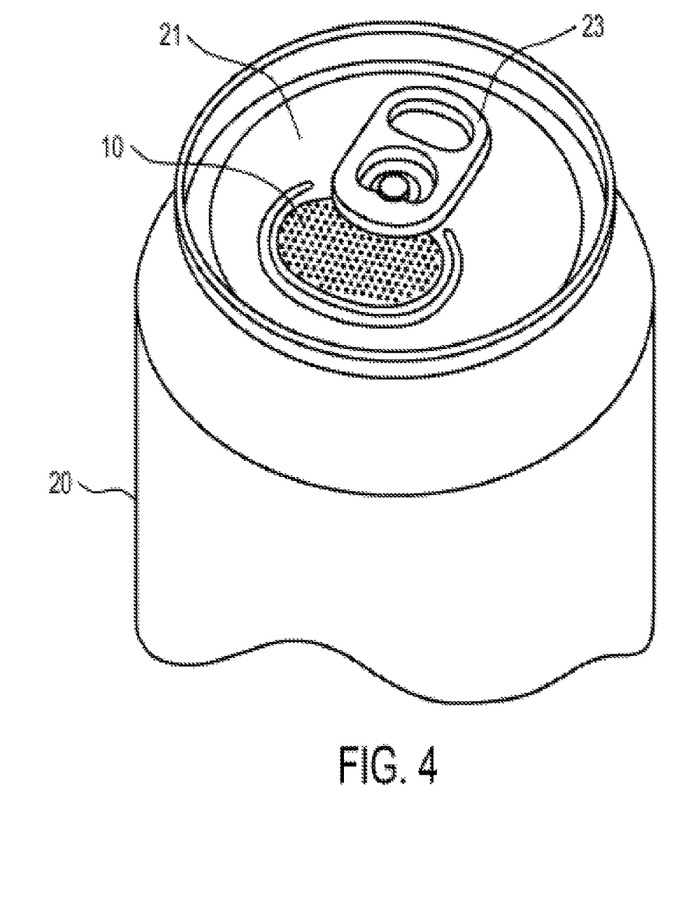
FIG. 4 illustrates another instance of a scented attachment of FIG. 3B.

FIG. 4 illustrates an instance of a scented attachment for a container 20 that is configured as a can. The scented attachment 10 is positioned on a top portion 21 of the can 20 next to the opening mechanism 23. The scented attachment 10 may be previously associated to the can 20 or may be a separate element that is obtained and attached to the can, such as immediately prior to use of the can. The scented attachment 10 may be configured such and associated with the opening mechanism 23 of the can 20 such that by opening the can the scent is released by the attachment 10.

Figure 5:
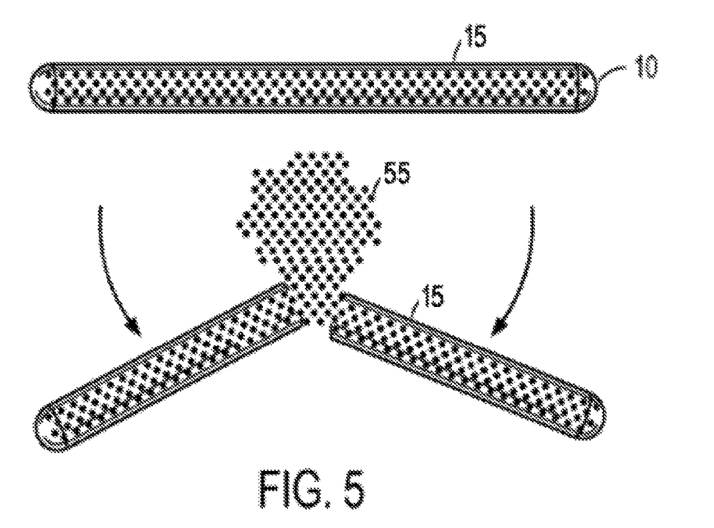
FIG. 5 illustrates a scented capsule.

FIG. 5 illustrates a scented attachment for a scented capsule, wherein the attachment 10 includes a main body 15 and a scented material 55 therein. The main body 15 may be such that when cracked one or more pores forms and the scent 55 is released there from.

In one aspect, the subject invention is directed to a protective sleeve system. In certain embodiments, the protective sleeve system is configured for both holding and protecting a held container. Accordingly, in certain embodiments, the protective sleeve system includes a protective sleeve (such as described above), which includes a tubular body, configured for holding a container, and at least a first opening, adapted for receiving the container, and in addition to the protective sleeve, the protective sleeve system may include a suitable container, such as those described above, for instance, a bottle, can, or other food storage element that is adapted to be fit and/or held within the protective sleeve.

For instance, in certain instances, the scented attachment may be included in a system that includes a suitable container, such as a glass or plastic bottle. For example, the container may be a water or sports drink bottle, or the like. The attachment may be previously associated with the bottle or may be a separate element that is meant to be attached to the container by the user of the container prior to use. The attachment may be a substrate having a scented surface having a cover thereon and may include an adhesive surface additionally having a cover thereon. The cover over the adhesive may be removed and the substrate associated with the container by the user. The cover covering the scented surface may then be removed by the user prior to consuming the drink or food item therein. In an alternative embodiment, the attachment may be a ring that is configured for being slid over an end of the container and associated thereby with the container, for instance, a neck of the container, e.g., by a user.

While various instances have been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the invention. All such modifications are intended to be within the scope of the claims appended hereto.

What is claimed is:

1. A system for containing and delivering a scent during consumption of a beverage, the system comprising:
    a drinking container having a main body to contain a fluidic beverage and a neck that is narrower than the main body, the drinking container having an opening at an end of the neck opposite the main body to dispense fluidic beverage out of the drinking container;
    a cap removably attachable to the drinking container to enclose the opening of the neck of the drinking container to contain the fluidic beverage within the drinking container when attached, the cap being removable from the opening of the drinking container to allow the fluidic beverage to be dispensed from the drinking container when unattached; and
    a scented attachment ring that is dimensioned to fit around the neck of the drinking container proximate the opening of the drinking container, the scented attachment ring is attached on a surface to the cap and is removably associated with the cap when the cap is attached to the drinking container, wherein the scented attachment ring is removably associated with the drinking container, the scented attachment ring including a volatile scented agent incorporated in the scented attachment ring and operable to generate a scent capable of stimulating an olfactory sensation of a user including during consumption of the fluidic beverage when the cap is removed from the drinking container and separated from the scented attachment ring,
    wherein the system is operable to lock in the scent generated by the scented attachment ring based on engagement of the cap and the drinking container when the cap is attached, and to release the scent to an environment proximate the opening of the drinking container when the cap unattached.

2. The system of claim 1, wherein the scented attachment ring includes a matrix to incorporate the volatile scented agent, the scented attachment ring including a shape having a plurality of sides such that at least two sides of the scented attachment ring are exposed to release the scent.

3. The system of claim 1, wherein the scented attachment ring is stretchable.

4. The system of claim 3, wherein the scented attachment is operable to stretch such that the scented attachment ring is changeable from a first diameter to a second diameter larger than the first diameter when stretched.

5. The system of claim 4, wherein the scented attachment ring is reversibly stretchable, such that the scented attachment ring is operable to return from the second diameter to the first diameter.

6. The system of claim 5, wherein the scented attachment ring is configured to expand so as to allow the scented attachment ring to stretch around contours of the drinking container to be received on and snuggly fit around the neck.

7. The system of claim 1, wherein the scented attachment ring includes a structure that is flat or tubular and includes an opening through which the neck of the drinking container is insertable.

8. The system of claim 1, wherein the scented attachment ring is configured as a separable element of the system that is removably attachable to the drinking container by the user.

9. The system of claim 1, wherein the scented agent comprises a gel.

10. The system of claim 1, wherein scented agent comprises a fragrant oil.

11. The system of claim 10, wherein the fragrant oil comprises one or more of a citrus oil, a mint oil, an anise oil, a cardamom oil, a cinnamon oil, a clove oil, a coriander oil, an eucalyptus oil, a fennel oil, a lemongrass oil, or a nutmeg oil.

12. The system of claim 11, wherein the citrus oil comprises an oil selected from the group consisting of a lemon oil, a lime oil, a neroli oil, and an orange oil; or wherein the mint oil comprises an oil selected from the group consisting of a peppermint oil and a spearmint oil.

13. The system of claim 1, wherein the system is configured to release the scent to the environment to augment a perceived taste of the fluidic beverage when drank by the user from the drinking container.

14. The system of claim 1, wherein the scented attachment ring includes a plastic with an integrated scented oil.

15. The system of claim 1, wherein the scented attachment ring includes a color.

16. The system of claim 1, wherein the scented attachment ring includes a diameter length in a range of 20 mm to 40 mm.

17. The system of claim 1, wherein the scented attachment ring is a single piece from a unitary material.

18. The system of claim 1, wherein the scented attachment ring is formed by compression or injection molding.

19. The system of claim 1, wherein the fluidic beverage includes one or more of water, soda, a liquid nutrient, an electrolyte, a sports drink, or alcohol.

* * * * *